United States Patent [19]

Stoddard et al.

[11] Patent Number: 4,953,548

[45] Date of Patent: Sep. 4, 1990

[54] LASER RESISTANT VENTILATING DEVICE WITH LOCKING FERRULE

[75] Inventors: Philip V. Stoddard, Greenwich, N.Y.; Craig J. Bell, Winchester, N.H.; Donald R. Schneider, Cambridge, N.Y.

[73] Assignee: Mallinckrodt, Inc., St. Louis, Mo.

[21] Appl. No.: 266,666

[22] Filed: Nov. 3, 1988

Related U.S. Application Data

[63] Continuation-in-part of Ser. No. 9,747, Feb. 2, 1987, Pat. No. 4,834,087.

[51] Int. Cl.$^5$ .................. A61M 16/04; A61M 25/00; A61M 29/02; A62B 9/00
[52] U.S. Cl. .................. 128/207.14; 128/207.15; 128/207.16; 604/101; 604/103
[58] Field of Search .................. 285/382; 128/207.14, 128/207.15, 200.26, 207.16; 604/101, 103

[56] References Cited

U.S. PATENT DOCUMENTS

| | | | |
|---|---|---|---|
| 601,591 | 3/1898 | Sherman | 285/256 |
| 1,296,222 | 3/1919 | Russ | 29/237 |
| 1,398,634 | 11/1921 | Eastman | 285/256 |
| 1,889,711 | 11/1932 | Talley et al. | 285/382 |
| 2,209,239 | 7/1940 | Sterzenbach | 285/382 |
| 2,211,008 | 11/1940 | Goldberg | 285/256 |
| 2,456,048 | 12/1948 | Carpenter | 285/382 |
| 3,123,072 | 3/1964 | Bellamy, Jr. | 604/263 |
| 3,376,060 | 4/1968 | Tomioka | 285/382 |
| 3,549,180 | 12/1970 | MacWilliam | 285/256 |
| 3,854,484 | 12/1974 | Jackson | 128/207.15 |
| 3,884,242 | 5/1975 | Bazzell et al. | 128/207.15 |
| 3,931,822 | 1/1976 | Marici | 128/207.15 |
| 4,022,217 | 5/1977 | Rowean | 128/207.15 |
| 4,063,561 | 12/1977 | McKenna | 128/207.15 |
| 4,091,816 | 5/1978 | Elam | 128/207.15 |
| 4,156,428 | 5/1979 | Henkin | 128/207.15 |
| 4,230,108 | 10/1980 | Young | 128/207.15 |
| 4,235,239 | 11/1980 | Elam | 128/207.15 |
| 4,289,128 | 9/1981 | Rüsch | 128/207.15 |
| 4,310,184 | 1/1982 | Campbell | 285/382 |
| 4,324,235 | 4/1982 | Beran | 128/207.15 |
| 4,328,983 | 5/1982 | Gibson | 285/382 |
| 4,341,210 | 7/1982 | Elam | 128/207.15 |
| 4,357,990 | 11/1982 | Melnyk | 285/382 |
| 4,377,164 | 3/1983 | Sabbota | 128/207.14 |
| 4,378,796 | 4/1983 | Milhaud | 128/207.15 |
| 4,402,684 | 9/1983 | Jessup | 128/207.14 |
| 4,423,725 | 1/1984 | Baran et al. | 128/207.15 |
| 4,489,722 | 12/1984 | Ferraro et al. | 128/207.15 |
| 4,504,269 | 3/1985 | Durand | 604/272 |
| 4,611,832 | 12/1986 | Matsuoka et al. | 285/55 |
| 4,649,913 | 3/1987 | Watson | 128/207.15 |
| 4,658,812 | 4/1987 | Hatzenbuhler et al. | 128/207.14 |
| 4,769,897 | 9/1988 | Moseman | 283/382 |
| 4,834,087 | 5/1989 | Coleman et al. | 128/207.14 |

OTHER PUBLICATIONS

"Norton Endotracheal Tube", Norton & DoVos, Annals of Otology, Rhinology, and Laryngology, Jul.-Aug. 1978, vol. 87, #4, pp. 554–557.

*Primary Examiner*—Edgar S. Burr
*Assistant Examiner*—Kimberly L. Asher
*Attorney, Agent, or Firm*—Bernard, Rothwell & Brown

[57] ABSTRACT

A liquid-filled sealing cuff of an airtight surgical ventilating device is protected from laser-effected damage during laser surgery by a liquid-containing barrier cuff positioned between an area of the laser surgery and the liquid-filled sealing cuff. The body of the surgical ventilating device is formed of a matte-finished flexible metal tube in the area of the laser surgery to resist damage by laser beam impact and to dispose highly unfocused light when a surgical laser beam is directed against the outer surface of the metal tube. A locking ferrule prevents disengagement of an atraumatic insertion tip of the device from the flexible metal tube.

15 Claims, 3 Drawing Sheets

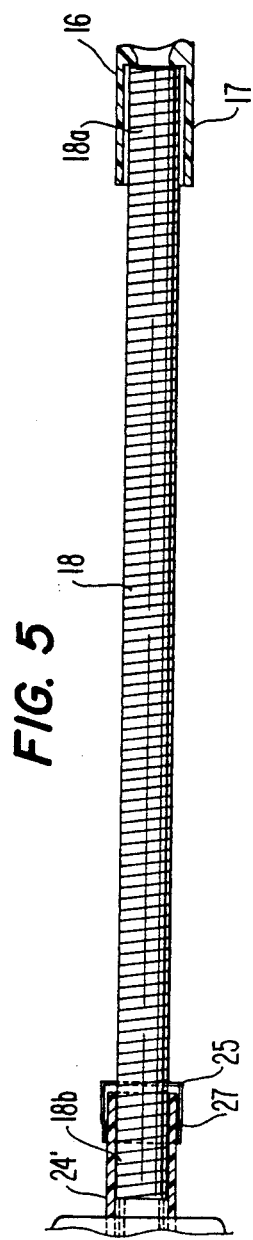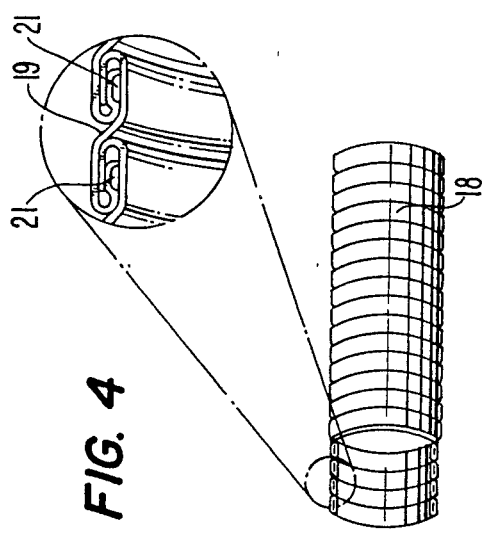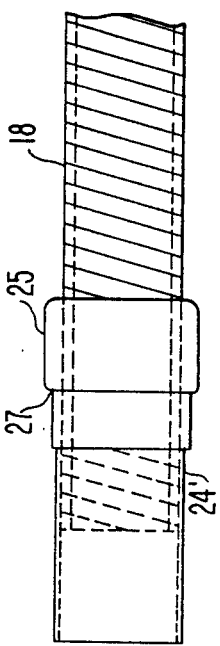

LASER RESISTANT VENTILATING DEVICE WITH LOCKING FERRULE

BACKGROUND OF THE INVENTION

Cross-Reference to Related Application

The present application is a continuation-in-part of copending Ser. No. 009,747, filed Feb. 2, 1987, now U.S. Pat. No. 4,834,087.

1. Field of the Invention

The present invention relates to a device employed for ventilating a patient during surgical use of a laser in a patient's airway.

2. Description of the Background Art

Endotracheal tubes for controlling ventilation of a patient during surgery are known in the art. Such devices generally include a tubular body for conveying the ventilation and anesthesia gases to and from a patient's lungs. In order to provide a tight seal with the trachea for controlled ventilation, a balloon or cuff typically is provided near a distal end of the endotracheal tube, the cuff being inflatable from outside the patient by means of an auxiliary conduit. In order to minimize the possibility of damaging a respiratory tract into which a ventilation device is inserted, such devices usually are constructed of flexible polymeric material.

Laser microlaryngeal surgery is increasingly being employed for treatment of localized laryngeal and tracheal lesions. There are several known types of surgical lasers, including ruby, argon, helium-neon, Nd-YAG and carbon dioxide lasers. However, the carbon dioxide laser appears best for the removal of laryngeal papillomas, polyps, nodules, cysts and the like, since carbon dioxide lasers produce $10.6\mu$ lightwaves which are absorbed by biological tissue, destroying targeted cell membranes and vaporizing cellular contents.

During laser microlaryngeal surgery, an unobstructed, binocular view of a lesion is provided. This provides advantages over other known types of laryngeal surgery, such as diathermy and cryosurgery, which utilize a probe that may obscure a surgeon's view of the operative field. In addition, lasers provide a relatively bloodless field, and post-operative edema is usually absent because the area treated by laser is sharply defined. Ideally, laser surgery leaves the surrounding tissue totally unaffected, allowing rapid healing with minimal post-operative scarring.

One consideration of microlaryngeal surgery is that the operative field is shared by the anesthesiologist and the surgeon. This can be addressed by using an endotracheal tube having an outer diameter sufficiently small to permit the surgery to take place while having an inflatable cuff large enough to make a seal. Alternatively, the surgery can occur with no tube in the airway with patient ventilation and anesthetic gas delivery given during interruptions in surgery via a mask.

There are disadvantages to having no tube in the airway. These include: lack of complete airway control, the possibility of apnea or hypoventilation with secondary cardiac arrythmias, laryngospasm from too light a plane of anesthesia, non-immobilized vocal cords, and exhalation of potent anesthetic gases through the open mouth of the patient making scavenging of these gases difficult.

Although performing microlaryngeal surgery with no tube in the airway is undesirable for reasons listed above, problems also arise during laser microlaryngeal surgery when employing an endotracheal tube. These problems typically involve damage caused by the laser of one or both of the endotracheal tube and inflatable cuff. Laser damage to the ventilation device may result in loss of airway management, burning of respiratory tissue, and the production of toxic fumes.

One method which has been proposed to reduce the risk of damaging the endotracheal tube during laser surgery is to wrap the endotracheal tube with metallic tape. However, wrapping a tube in metal tape is time consuming, and rough edges of the tape may abrade and injure the mucosa of the pharynx and larynx. In the event of a poor wrapping job, the possibility exists that uncovered areas can be ignited, as does the possibility that loose pieces of tape can be aspirated. Wrapped metal tape increases the possibility of a kink developing in the tube, and inadvertent mucosal damage may occur due to reflection of the laser beam off the tape.

Another proposed method for reducing the risk of ignition of an endotracheal tube is to wrap the tube in wet muslin. However, this also is time consuming, and the muslin adds additional bulk to the tube. Additionally, the muslin may dry out and ignite during surgery.

Yet another proposed method for reducing the risk of ignition of an endotracheal tube is to coat the tube with dental acrylic. However, dental acrylic rigidifies the tube and is not completely impenetrable by surgical lasers. The dental acrylic further adds undesired bulk to the tube and is time consuming to apply.

Metal tracheal tubes also have been utilized to avoid ignition of the tube during laser surgery, but problems with the use of metal tracheal tubes have been encountered. These problems include tissue damage brought about by insertion of rigid metal tubes, and inadvertent mucosal damages due to reflection of the laser beam off of the metal tube. Metal tracheal tubes typically have large external diameters which precludes their use with pediatric patients and patients with tracheal stenosis, and generally have no inflatable cuff for creating an air-tight seal. Moreover, the currently available flexible metal tracheal tubes typically are constructed such that the wall of the tube is not air tight.

Venturi ventilation has been employed during laser microlaryngeal surgery, but this may poses problems such as pneumothorax, pneumomediastinum, stomach inflation, aspiration of secretions, complete respiratory obstruction, and dehydration of mucosal surfaces.

The use of metallically filled polymers for tube construction also has been suggested to reduce the risk of ignition of endotracheal tubes. However, proposed metallically filled polymers provide only minimal resistance to penetration by laser beam impact (especially in $O_2/NO_2$ enriched atmospheres), and are generally quite expensive.

There remains a need in the art for a surgical ventilation device which is resistant to laser-caused dysfunction during laser surgery.

SUMMARY OF THE INVENTION

In accordance with the present invention, a surgical ventilation device resistant to laser-caused dysfunction during laser surgery defines a continuous gas passageway for passage of ventilation gases during surgery. The device includes a beveled distal end to facilitate insertion into a patient's airway, the distal end defining a portion of the continuous gas passageway. A proximal end is also provided for connecting the continuous gas passageway to a source of gas. The surgical ventilating device of this invention includes an airtight flexible metal tube having an airtight wall portion connecting the distal end and the proximal end of the ventilating device. The metal tube is resistant to damage by a surgical laser and has a matte outer surface for dispersing unfocused light when a surgical laser beam is directed against the outer surface of the device. The metal tube defines a substantial portion of the continuous gas passageway. A lower, liquid-inflatable polymeric sealing cuff and an upper, liquid-inflatable barrier cuff are connected to and longitudinally disposed along a lower polymeric tubing assembly at the distal end of the device, the lower cuff being situated between the upper cuff and the distal end. The lower polymeric tubing assembly, with upper and lower cuffs, is connected to the metal tube by a locking ferrule that compresses a proximal end section the polymeric tubing assembly against the metal tube so as to prevent disengagement. The lower cuff is inflated with liquid to bring the lower cuff into sealing contact with a patient's airway and thereby prevent a gas leakage between the lower cuff and the airway. The upper cuff is inflated with liquid for bringing the upper cuff into contact with airway to thereby shield the lower cuff from damage caused by laser energy directed toward the lower cuff.

BRIEF DESCRIPTION OF THE DRAWINGS

FIG. 4 is a perspective view in partial cross-section and with a portion enlarged of a segment of a metal tube of a surgical ventilating device according to one embodiment of the invention.

FIG. 5 is a partly schematic elevation view with portions broken away of a ventilating device according to the invention showing interconnection of tubing elements according to one embodiment.

FIG. 7 is an enlarged, partly schematic, elevation view with portions broken away and portions removed, showing interconnection of the lower portions of a ventilating device with a locking ferrule according to a preferred embodiment of the invention.

DETAILED DESCRIPTION OF THE PREFERRED EMBODIMENT

Figure 1:
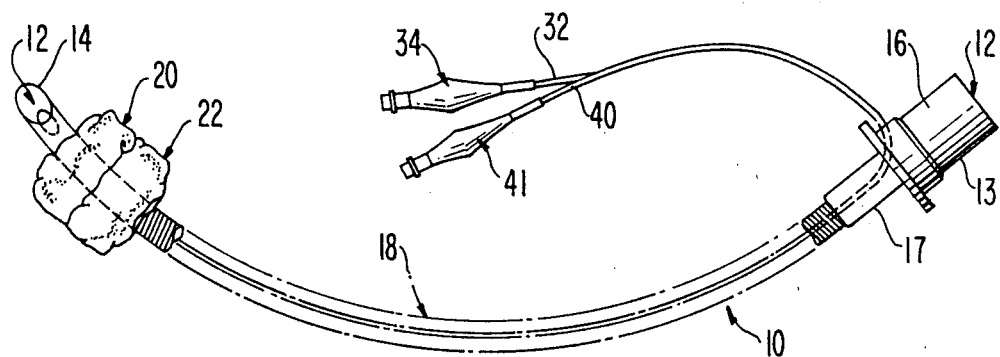
FIG. 1 is an elevation view, partly schematic, of a laser-resistant surgical ventilation device in accordance with the present invention.
Figure 2:
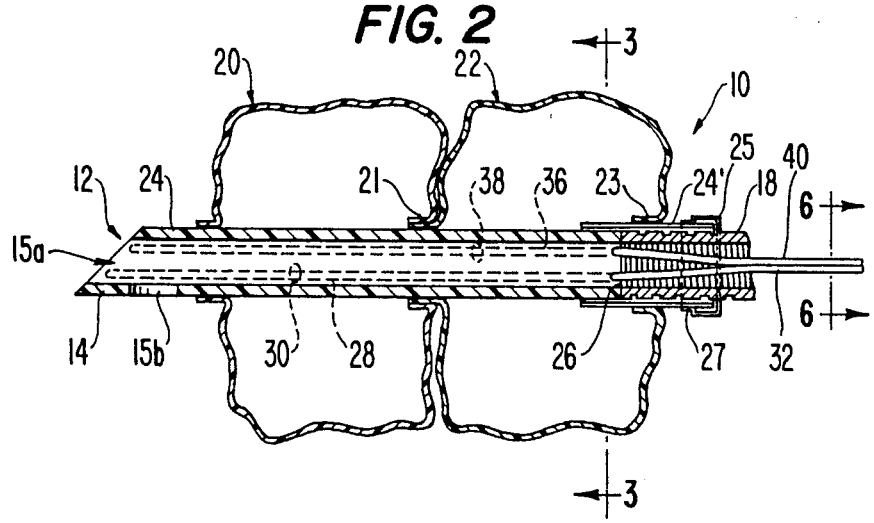
FIG. 2 is an enlarged elevation view, partly schematic and in partial cross-section, of the laser-resistant double-cuffed distal end of the surgical ventilation device shown in FIG. 1.

The endotracheal tube 10 shown in FIGS. 1 and 2 is a surgical ventilation device which is resistant to laser-caused dysfunction during laser surgery. The device defines a continuous gas passageway 12 for passage of ventilation gases (including anesthetic and respiratory gases) during surgery.

Endotracheal tube 10 includes a distal end 14 with a beveled tip to facilitate insertion into a human trachea, and defines a portion of the continuous gas passageway 12.

Endotracheal tube 10 further includes a proximal end 16 for connecting the continuous gas passageway 12 to a source of gas (not shown).

A flexible metal tube 18 having an airtight wall portion is disposed between the distal end 14 of the endotracheal tube and the proximal end 13 of the ventilation device. The flexible metal tube 18 is resistant to damage by a surgical laser, and as can be seen in FIG. 1, metal tube 18 defines a substantial portion of the continuous gas passageway 12. The proximal end 13 of the ventilation device is connected to the metal tube 18 by an upper polymeric tubing 17 disposed over the proximal end of metal tube 18 to form an airtight fit.

In order to prevent inadvertent and unintended damage to a patient's tissues during surgery due to reflection of a laser beam off of the metal tube, metal tube 18 is provided with a matte outer surface for dispersing unfocused light when a surgical laser beam is directed against the outer surface of the metal tube. The airtight metal tube 18 may be of any suitable construction to permit flexibility, such as a helically convoluted metal hose, a segmented flexible metal hose or corrugated bellows, and is characterized by substantial continuity from one end to another so as not to provide laser-penetrable apertures in the sidewall of the metal tube.

Advantageously, the flexible metal tube 18 is constructed of stainless steel for corrosion resistance. The matte exterior finish of the flexible metal tubing reflects a highly unfocused beam, which minimizes the potential of inadvertently damaging tissue.

One suitable construction for metal tube 18 is shown in FIG. 4. According to this embodiment, metal tube 18 starts out as a thin stainless steel ribbon (i.e., 0.0035" thick and 0.212" wide). This ribbon is fed through a die set to form a helically convoluted hose or tube. The die crimps the ribbon 19 back on to itself as shown in FIG. 4. At the same time ribbon 19 is being formed in the die, a fine metallic filament 21 is fed into an overlapping channel between adjacent crimped ribbon portions. Metallic filament 21 has a lower melting temperature than the metallic composition of ribbon 19. The formed strip wound metal hose is heat treated in order to melt the metallic filament 21 and thus hermetically seal the seam.

Figure 3:
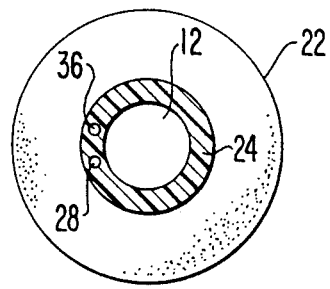
FIG. 3 is a cross-sectional view along line 3—3 of FIG. 2.

Referring back to FIGS. 1–3, approximate the distal end 14 of endotracheal tube 10 is located a lower liquid-inflatable elastomeric sealing cuff 20 with lower proximal cuff shoulder 21 inverted to reduce the required intratracheal length, and an upper liquid-inflatable barrier cuff 22 with upper proximal cuff shoulder 23 inverted to both reduce the required intratracheal length and to minimize the exposure of polymeric materials. The ventilating device is airtight along its length from the proximal end 13 thereof to cuffs 20 and 22.

The lower and upper cuffs 20 and 22, respectively, are mounted on the outer surface of a lower polymeric tubing assembly comprised of a tubular polymeric distal tip member 24 and a tubular polymeric sleeve 24'. As shown in FIGS. 1 and 2, the lower cuff 20 is positioned between the upper cuff 22 and the distal end 14 of the endotracheal tube 10.

The polymeric portions of the ventilation device, including tubing assembly 24, 24' and upper polymeric tubing 17 (shown in FIGS. 1 and 5), may be constructed of any suitable biocompatible material, such as biocompatible polyvinyl chloride, polyurethane, silicone and the like.

Tip member 24, at the distal end 14 of endotracheal tube 10 is an atraumatic insertion tip including a longitudinal ventilation opening 15a, and advantageously includes a transverse ventilation opening 15b in the event that the longitudinal opening 15a is blocked during use.

In the embodiment shown in FIGS. 1 and 2, the tip member 24 is received within the polymeric sleeve 24' and attached thereto by any suitable means, such as an ultraviolet (U.V.) light-cured adhesive, chemical weld or glue. The polymeric sleeve 24' comprises a proximal end section of the lower polymeric tubing assembly, within which is received the distal end of the metal tube 18, thus connecting the distal end 26 of metal tube 18 with the proximal end section of the lower polymeric tubing assembly.

Figure 8:
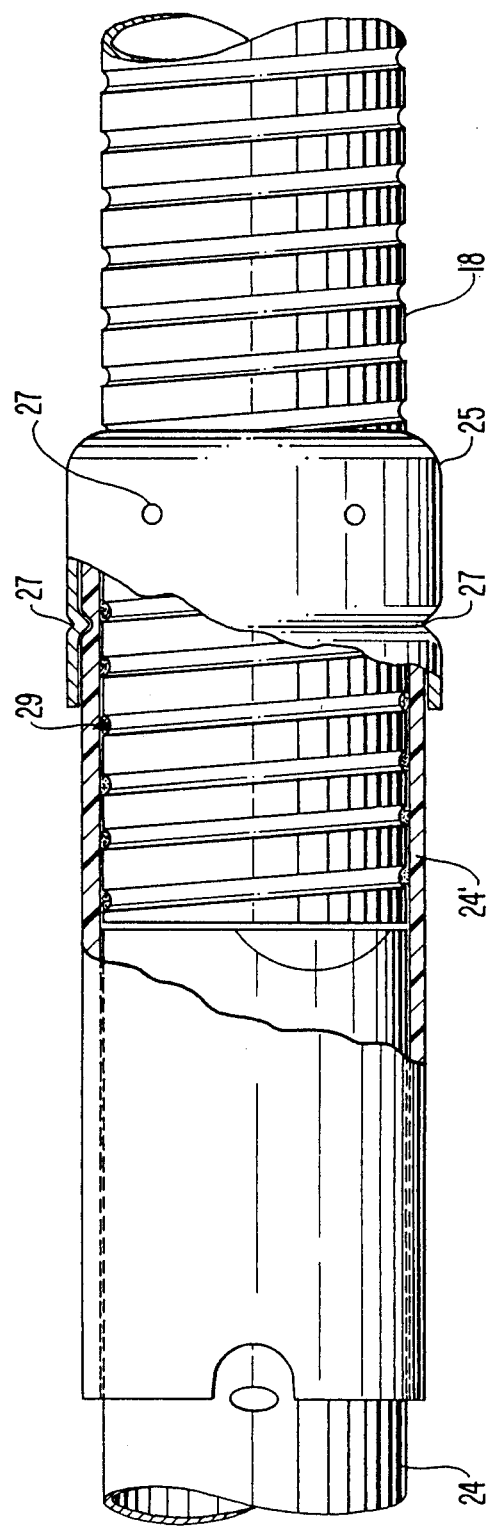
FIG. 8 is an enlarged, partly schematic, elevation view with portions broken away and portions in cross-section, showing interconnection of the lower portions of a ventilating device with a locking ferrule according to another embodiment of the invention.

By the present invention, a locking ferrule is provided for preventing disengagement of the lower polymeric tubing assembly from the metal tube 18. At least a portion of the locking ferrule is pinched inwardly so as to compress the proximal end section of polymeric sleeve 24' against the metal tube 18. In the embodiment preferred shown in FIGS. 2, 5 and 7, the locking ferrule 25 of the invention is an annular metal collar that extends around the proximal end section of polymeric sleeve 24'. An annular crimp 27 is provided by compressing (i.e., crimping) the locking ferrule on its outside diameter, which reduces the outside diameter of the locking ferrule along the crimp and forms a mechanical bond between the proximal end section of sleeve 24' and spirals of metal tube 18, thereby preventing disengagement. A glue or other adhesive such as U.V. curable adhesive 29 (shown in FIG. 8) can be used to further connect and seal the distal end of metal tube 18 to sleeve 24'.

Although the annular crimp 27 discussed above with reference to FIGS. 2, 5 and 7 is the preferred embodiment, other embodiments that pinch the locking ferrule inwardly may be used. For example, in FIG. 8, a locking ferrule 25' is disclosed which includes a plurality of inwardly pinched depressions 27' that "stake" the locking ferrule 25' to the metal tube 18 while compressing the proximal end section of sleeve 24' against the metal tube 18 to prevent disengagement therefrom. As previously discussed, a glue or other adhesive 29 can be used to further connect and seal the distal and of metal tube 18 to sleeve 24'. An annular crimp as detailed in FIG. 7 is the preferred embodiment over staking, since the annular crimp has been found to form a stronger mechanical bond and provide a better seal than staking.

In the embodiments shown, cuffs 20 and 22 are polymeric, and attached to tip member 24 by any suitable means such as by heat sealing. Suitable materials for forming the polymeric cuffs include polyvinyl chloride, polyurethane, silicone and the like.

Means are provided for inflating the lower sealing cuff 20 to bring the lower cuff 20 into sealing contact with a patient's trachea and thereby prevent leakage of gas between the lower cuff 20 and the trachea. Although sealing cuff 20 can be inflated with a gaseous fluid, in the preferred embodiment, sealing cuff 20 is inflated with an aqueous liquid. To effect inflation of sealing cuff 20, a first inflation lumen 28 is provided in the lower polymeric tip member 24, lumen 28 being in communication with lower cuff 20 by means of port 30. See FIGS. 2 and 3.

Inflation lumen 28 is connectable with a fluid source for inflation of lower cuff 20 by means including a first conduit 32.

Conduit 32 is disposed within metal tube 18 for protection against laser damage during surgery, and connects lower cuff 20 with a first valve 34 for connecting the first conduit 32 with a liquid source (not shown) and for controlling inflation and deflation of lower cuff 20.

Means are provided for inflating the upper barrier cuff 22 with an aqueous liquid for bringing the upper cuff 22 into contact with a patient's trachea to thereby shield the lower cuff 20 from damage caused by laser energy directed towards the lower cuff. Upper cuff 22 shields the lower cuff from damage by a surgical laser by being positioned between an area of laser surgery (e.g., in an area adjacent metal tube 18) and the fluid-filled sealing cuff 20.

The upper barrier cuff 22 is inflated by means including a second inflation lumen 36 in the lower polymeric tip member 24. The second inflation lumen 36 is in communication with the upper cuff 22 through port 38. The second inflation lumen 36 is connectable with a second liquid source for inflation of upper cuff 22 by means including a second conduit 40 disposed within metal tube 18 for protection against laser damage. The second conduit 40 connects the second inflation lumen 36 with a second valve 41 in communication with a liquid source (not shown) for controlling inflation and deflation of upper cuff 22.

In the embodiment shown in FIG. 1, the first and second conduits 32 and 40 exit metal tube 18 through a standard 15 mm connector 16 for connecting to a source of gas. The connector 16 can be constructed of rigid or semi-rigid biocompatible polymeric materials such as PVC and ABS. The connector 16 is attached to metal tube 18 by any suitable means, such as glue or other adhesive. If desired connector 16 can be attached to metal tube 18 in the same manner as lower polymeric sleeve 24'.

Figure 6:
FIG. 6 is a cross-sectional view of a connected pair of liquid conduits for inflating elastomeric cuffs of the surgical ventilation device shown in FIG. 1.

Conduits 32 and 40 are adhered together as shown in FIG. 6 by means of a solvent or by extruding them as one. This, along with the orientation of lumens 36 and 28, allow easy passage of suctions and stylets through gas passageway 12. Conduits 32 and 40 exit through a port in connector 16. They are anchored in this port by means such as glue.

In the embodiment shown in FIG. 5, the ends 18a and 18b of metal tube 18 are partially deconvoluted. The increase in distance between convolutions of metal tube 18 at the ends provides a means for an adhesive to mechanically hold onto the stainless steel tubing. The proximal end 18a of the tube 18 has adhesive applied to it 360° around the outer diameter thereof and the upper polymeric tubing 17, such as a standard 15 mm connector, is slid over the metal tube. The distal end 18b of tube 18 has adhesive applied to it 360° around the outer diameter thereof and lower polymeric sleeve 24' expanded and placed on the metal tube. A plastic atraumatic tip including ventilation openings 15a and 15b (as shown in FIG. 2) can be solvent bonded to the internal diameter of the lower polymeric sleeve 24' such that it butts up against the end of the metal tube. Locking ferrule 25 is crimped (and/or staked, if desired) about the proximal end section of sleeve 24' to prevent disengagement from metal tube 18.

After tracheal tube 10 is intubated (i.e., inserted into a patient's trachea), the cuffs 20 and 22 are fluid filled with sterile isotonic saline solution. The lower sealing cuff 20 is pressurized to maintain a tracheal seal, and the upper bearing cuff 22 is filled, but advantageously not to the point of creating any substantial pressure (e.g., filled to near atmospheric pressure). When fluid in the upper barrier cuff is at or near atmospheric pressure, a single perforation of the barrier cuff 22 by a surgical laser does not result in substantial fluid drainage from barrier cuff 22.

The probability of hitting a cuff during a single laser laryngeal surgery procedure can be determined from Fried, M.P., "A Survey of the Complications of Laser Surgery", *Arch. Otolaryngology*, 110:31–34 (1984). The probabilities have been calculated as follows:

P (hitting cuff 1 time)=0.06173
P (hitting cuff 2 times)=0.00381
P (hitting cuff 3 times)=0.00024
P (hitting cuff 4 times)=0.00001

Since a single laser perforation of the barrier cuff 22 does not result in a substantial amount of fluid drainage due to about atmospheric pressure in barrier cuff 22, it can be seen that barrier cuff 22 provides a substantial amount of protection for sealing cuff 20 and distal end 14 of tip member 24. Further, water is an excellent absorber of the $10.6\mu$ wavelength of a carbon dioxide laser such that surface molecules of the water are boiled off and the laser energy dissipated providing further protection for sealing cuff 20. The water in the barrier cuff 22 also eliminates virtually any threat of ignition and burning of the polymeric cuffs.

According to one embodiment, the barrier cuff may be filled with a colored aqueous solution which will leak out if the cuff is perforated and thereby visually indicate that the cuff has been perforated. An example of a suitable dye for coloring the aqueous solution is methylene blue. Other types of dyes may also be used.

It can be seen that the present invention provides a stable surgical ventilation system which is highly resistant to laser-caused dysfunction during laser surgery. The matte-finished flexible metal tube is impenetrable by a surgical laser and reflects a highly out-of-focus beam to preclude inadvertent damage to tissue. The locking ferrule prevents disengagement of the metal tube from the lower polymeric tubing carrying the double-cuff system. The liquid-filled barrier cuff provides protection to the tracheal sealing cuff against damage by a laser beam impact. The double-cuff system allows the user at least one cuff hit that will not cause loss of protection by the barrier cuff and lead to tracheal tube dysfunction. This, along with the very low probability that the cuff will be hit again and the stability of the system resulting from the locking ferrule, provides for safe and effective airway control during laser surgery.

Since many modifications, variations and changes in detail may be made to the described embodiments, it is intended that all matter in the foregoing description and shown in the accompanying drawings be interpreted as illustrative and not in a limiting sense.

What is claimed is:

1. A surgical ventilation device which is resistant to laser-caused dysfunction during laser surgery, comprising a ventilation device defining a continuous gas passageway for passage of ventilation gases during surgery, the device further comprising:
    (a) a distal end for insertion into a patient's airway, the distal end defining a portion of said continuous gas passageway;
    (b) a proximal end for connecting the continuous gas passageway to a source of gas;
    (c) a flexible airtight metal tube connecting the distal end and the proximal end of the device, the metal tube being resistant to damage by a surgical laser and having a matte outer surface for dispersing unfocused light when a surgical laser beam is directed against said outer surface, the metal tube defining a substantial portion of said continuous gas passageway;
    (d) a lower liquid-inflatable cuff comprising means for making sealing contact with the patient's trachea and means for preventing leakage of gas between the lower cuff and the trachea, and an upper liquid-inflatable barrier cuff for contacting the patient's trachea, the lower and upper cuffs connected to and longitudinally disposed along the ventilation device at approximately the distal end of the device, the trachea-sealing lower cuff being disposed between the upper cuff and the distal end, the barrier cuff providing shielding means for the sealing cuff from damage by laser energy directed toward the sealing cuff;
    (e) a lower polymeric tubing assembly having an outer surface on which said lower and upper cuffs are mounted, the lower polymeric tubing assembly having a distal end which is the distal end of the ventilating device and a proximal end section within which is received a distal end of the metal tube, the ventilation device being airtight from the proximal end thereof to said cuffs on said lower polymeric tubing assembly;
    (f) a locking ferrule that extends around said proximal end section of the lower polymeric tubing assembly, at least a portion of the locking ferrule being pinched inwardly so as to compress the proximal end section of the lower polymeric tubing assembly against the metal tube and thereby prevent disengagement of the lower polymeric tubing assembly from the metal tube;
    (g) means for inflating the lower cuff with liquid to bring the lower cuff into sealing contact with a patient's airway to prevent leakage of gas between the lower cuff and the airway, the means for inflating the lower cuff including a first conduit disposed within the metal tube and protected thereby from laser damage, the first conduit being in communication with the lower cuff and connectable with a source of liquid for inflating the lower cuff; and
    (h) means for inflating the upper cuff with liquid, bringing the upper cuff into contact with said airway, and shield the lower cuff from damage caused by laser energy directed toward the lower cuff, the means for inflating the upper cuff including a second conduit disposed within the metal tube and protected thereby from laser damage, the second conduit being in communication with the upper cuff and connectable with a source of liquid for inflating the upper cuff.

2. The ventilation device of claim 1 wherein said locking ferrule is metal.

3. The ventilation device of claim 2 wherein said locking ferrule is crimped into place about said metal tube with the proximal end section of the lower polymeric tubing assembly compressed therebetween.

4. The ventilation device of claim 2 wherein said locking ferrule is staked into place about said metal tube with the proximal end section of the lower polymeric tubing assembly compressed therebetween.

5. The ventilation device of claim 1 further including adhesive between the meal tube and that portion of the lower polymeric tubing assembly that extends over the metal tube.

6. The ventilation device of claim 1 wherein said lower polymeric tubing assembly is comprised of a tubular polymeric distal tip member and a tubular polymeric sleeve that connects the tip member to the metal tube, said sleeve comprising said proximal end section of the lower polymeric tubing assembly.

7. The ventilation device of claim 1 wherein the metal tube is selected from the group consisting of helically convoluted metal hose, segmented flexible metal hose and corrugated bellows.

8. The ventilation device of claim 1 further including an upper polymeric tubing connecting the proximal end of the ventilation device to the metal tube.

9. A surgical ventilation device which is resistant to laser-caused dysfunction during laser surgery, comprising a ventilation device defining a continuous gas passageway for passage of ventilation gases during surgery, the device further comprising:
  (a) a lower liquid-inflatable elastomeric cuff comprising means for for making sealing contact with a patient's trachea and preventing leakage of gas between the lower cuff and the trachea, and an upper liquid-inflatable barrier cuff for contacting the patient's trachea, the lower and upper cuffs mounted on a lower polymeric tubing assembly approximate a distal end of the ventilation device, the trachea-sealing lower cuff between the upper cuff and the distal end of the device, the barrier cuff positioned to shield the sealing cuff from damage by laser energy directed toward the sealing cuff, the lower polymeric tubing assembly defining a portion of said continuous gas passageway, the distal end of the ventilation device for insertion into a patient's airway;
  (b) a flexible metal tube defining a substantial portion of said continuous gas passageway, the metal tube having an airtight wall portion with a distal end which is received within a proximal end section of the lower polymeric tubing assembly comprising means for connecting the lower polymeric tubing with a proximal end of the ventilation device, the proximal end of the ventilation device including means for connecting the ventilation device to a source of gas, the metal tube being resistant to damage by a surgical laser and having a matte outer surface for dispersing unfocused light when a surgical laser beam is directed against said outer surface, the ventilation device being airtight from the proximal end thereof to said cuffs on said lower polymeric tubing assembly;
  (c) a metal locking ferrule that extends around said proximal end section of the lower polymeric tubing assembly, at least a portion of the locking ferrule being pinched inwardly so as to compress the proximal end section of the lower polymeric tubing assembly against the metal tube and thereby prevent disengagement of the lower polymeric tubing assembly from the metal tube;
  (d) means for inflating the lower cuff with aqueous liquid to bring the lower cuff into sealing contact with a patient's trachea to prevent leakage of gas between the lower cuff and the trachea, the lower cuff inflating means including a first inflation lumen in the lower polymeric tubing, the first inflation lumen being in communication with the lower cuff and connectable with a liquid source for inflation of the lower cuff, the lower cuff inflating mens further including a first conduit in communication with the first inflation lumen for connecting the first inflation lumen with the liquid source, the first conduit disposed within the metal tube and protected thereby from laser damage, the lower cuff inflating means further including a first valve in communication with the first conduit for connecting the first conduit with the liquid source and for controlling inflation of the lower cuff; and
  (e) means for inflating the upper cuff with aqueous liquid for bringing the upper cuff into contact with said trachea to thereby shield the lower cuff from damage caused by laser energy directed toward the lower cuff, the upper cuff inflating means including a second inflation lumen in the lower polymeric tubing, the second inflation lumen being in communication with the upper cuff and connectable with a second liquid source for inflation of the upper cuff, the upper cuff inflating means further including a second conduit in communication with the second inflation lumen for connecting the second inflation lumen with the second liquid source, the second conduit disposed within the metal tube and protected thereby from laser damage, the upper cuff inflating means further including a second valve in communication with the second conduit comprising means for connecting the second conduit with the second liquid source and means for controlling inflation of the upper cuff.

10. The ventilation device of claim 9 wherein said locking ferrule is crimped into place about said metal tube with the proximal end section of the lower polymeric tubing assembly compressed therebetween.

11. The ventilation device of claim 9 wherein said locking ferrule is staked into place about said metal tube with the proximal end section of the lower polymeric tubing assembly compressed therebetween.

12. The ventilation device of claim 9 further including adhesive between the metal tube and that portion of the lower polymeric tubing that extends over the metal tube.

13. The ventilation device of claim 9 wherein said lower polymeric tubing assembly is comprised of a tubular polymeric distal tip member and a tubular polymeric sleeve that connects the tip member to the metal tube, said sleeve comprising said proximal end section of the lower polymeric tubing assembly.

14. The ventilation device of claim 9 wherein the metal tube is selected from the group consisting of helically convoluted metal hose, segmented flexible metal hose and corrugated bellows.

15. The ventilation device of claim 9 further including an upper polymeric tubing connecting the proximal end of the ventilation device to the metal tube.

* * * * *